US006444979B1

(12) United States Patent
Watanabe (10) Patent No.: US 6,444,979 B1
(45) Date of Patent: Sep. 3, 2002

(54) METHOD OF AND APPARATUS FOR SEARCHING FOR UNKNOWN SPECIMEN, AND RECORDING MEDIUM WITH RECORDED PROGRAM FOR SEARCHING FOR UNKNOWN SPECIMEN

(75) Inventor: Chuichi Watanabe, Fukushima (JP)

(73) Assignee: Frontier Laboratories Ltd., Fukushima (JP)

( * ) Notice: Subject to any disclaimer, the term of this patent is extended or adjusted under 35 U.S.C. 154(b) by 0 days.

(21) Appl. No.: 09/354,338

(22) Filed: Jul. 16, 1999

(30) Foreign Application Priority Data

Jul. 16, 1998 (JP) .......................................... 10-201596

(51) Int. Cl.⁷ .............................................. H01J 49/00
(52) U.S. Cl. ....................................... 250/282; 250/281
(58) Field of Search ................................ 250/282, 281; 364/498

(56) References Cited

U.S. PATENT DOCUMENTS

| 4,075,475 A | * | 2/1978 | Risby et al. ................. 250/282 |
| 4,517,461 A | * | 5/1985 | Crandall ...................... 250/282 |
| 5,438,194 A | * | 8/1995 | Koudijs et al. .............. 250/288 |
| 5,453,613 A | * | 9/1995 | Gray et al. .................. 250/281 |
| 5,672,869 A | * | 9/1997 | Windig et al. ............... 250/282 |
| 6,008,490 A | * | 12/1999 | Kato ........................... 250/282 |

OTHER PUBLICATIONS

"Basic Description of GC/MS Data Systems", Message, *Practical Aspects of Gas Chromatography*, pp. 146–153.
"Techniques of Combined Gas Chromatography/Mass Spectrometry: Applications of Organic Analysis", McFadden, pp. 240–241.
"Analysis of Plastics Using Polymer Data Library Search GC/MS System", Shimadzu Co., Application No. U146–0027.
"You are Now Expert in Pyrolysis GC/MS from Today", Shimadzu Co., Brochure 3111–08617–50ATD.
"Probability Method for Pyrolysis Gas Chromatographic Data Treatment and Elaboration of a Computer System for the Identification of Polymers", Ryabikova et al, *Journal of Chromatography*, 520 (1999), pp. 121–129.
"The Development of Pyrolysis Capillary GC System and an Approach to Polymer Characterization Using Personal Computer", Watanabe et al, Shimadzu Scientific Instrument, Feb. 1993.

\* cited by examiner

Primary Examiner—Kiet T. Nguyen
(74) Attorney, Agent, or Firm—Arent Fox Kintner Plotkin & Kahn, PLLC (57) ABSTRACT

An unknown polymer is pyrolyzed by a pyrolizer and a produced mixture of pyrolytic products is separated into the pyrolytic products by a separating column. The separated pyrolytic products are detected by a mass spectrometer to generate a chromatogram. Ion intensities contained in all total ion intensities making up peaks in the chromatogram are added, for each ion of the same mass, to plot a combined mass spectrum of the unknown polymer. Combined mass spectra of a plurality of known polymers are generated in the same manner as with the combined mass spectrum of the unknown polymer, and stored as a library. The library is searched for the combined mass spectrum of one of the known polymers which agrees with a high probability percentage with the combined mass spectrum of the unknown polymer.

5 Claims, 11 Drawing Sheets

FIG. 3 (a)
DETECTED DATA OF Scan 1307 (11.562 min.)

FIG. 3 (b)
DETECTED DATA OF Scan 1310 (11.586 min.)

FIG. 3 (c)
DETECTED DATA OF Scan 1313 (11.611 min.)

FIG. 6

MASS SPECTRUM OF PEAK D

FIG. 7 (a)   DATA LIBRARY #1

FIG. 7 (b)   DATA LIBRARY #2

FIG. 7 (c)   DATA LIBRARY #3

FIG. 10 (a) 4, 4' - (1 - methylethylidene) bisphenol

FIG. 10 (b) 4, 4' - (1 - methylethylidene) bisphenol

FIG. 10 (c) p - phenyl - carbanilic acid

FIG. 10 (d) [1, 1' - biphenyl] -3-yl - carbamic acid

METHOD OF AND APPARATUS FOR SEARCHING FOR UNKNOWN SPECIMEN, AND RECORDING MEDIUM WITH RECORDED PROGRAM FOR SEARCHING FOR UNKNOWN SPECIMEN

BACKGROUND OF THE INVENTION

1. Field of the Invention

The present invention relates to a method of and an apparatus for, and a recording medium with a recorded computer program for, searching for an unknown specimen, i.e., identifying an unknown polymer such as a plastic or synthetic resin.

2. Description of the Prior Art

It has heretofore been known to identify an unknown polymer by producing data of the unknown polymer according to a process (Py-GC/MS) which is a combination of pyrolysis gas chromatography (Py-GC) and mass spectrometry (MS), and comparing the produced data with a library. Specifically, the data of the unknown polymer are compared with data of known polymers stored in the library to search for the data of the known polymer which agree with the data of the unknown polymer.

Figure 5:
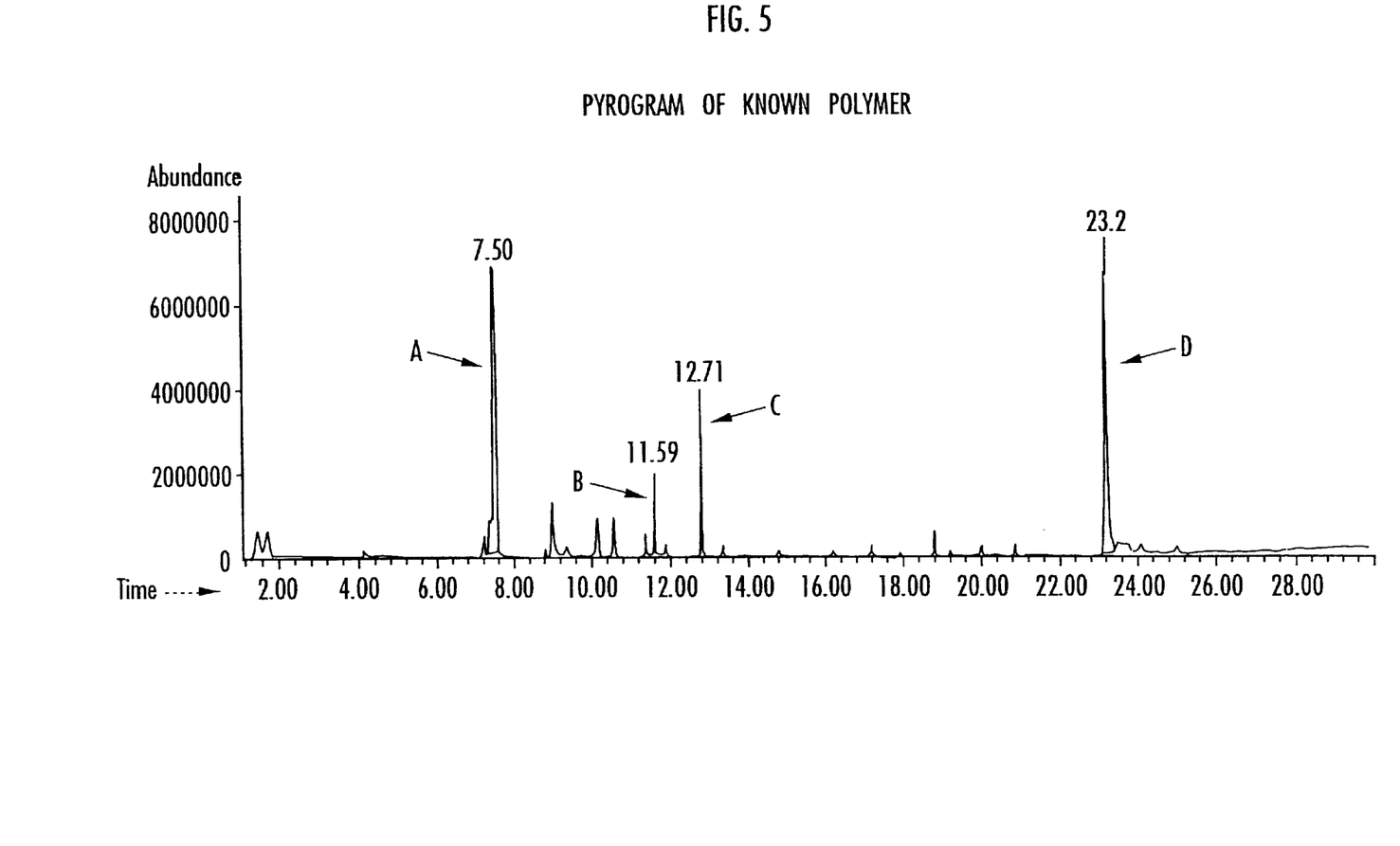
FIG. 5 is a pyrogram showing a result produced when a known polymer is analyzed by the apparatus shown in FIG. 1.

According to the Py-GC/MS process, a pyrolytic product of the unknown polymer is separated by a capillary column and analyzed by a mass spectrometer, which detects the intensities of molecular ions and fragment ions that are generated when an electron beam is applied to separated molecules. In the mass spectrometer, each time an electron beam is applied to the separated molecules for a predetermined period of time, e.g., 0.008 minute, one set of ion intensities is obtained as detected data. The detected ion intensities of each set are added to calculate a total ion intensity, and the total ion intensities of the sets are plotted successively at detected times, producing a pyrolysis gas chromatogram (pyrogram) as shown in FIG. 5 of the accompanying drawings.

The pyrogram itself may be compared with the pyrogram of a known polymer specimen to identify the unknown polymer. According to the Py-GC/MS process, however, it is customary to generate mass spectra of peaks of the pyrogram and search a library of mass spectra of known polymers based on the generated mass spectra.

For example, when the ion intensities of total ion intensities that make up portions corresponding to the maximum points of the peaks, as representative values of the total ion intensities, are arranged in the order of masses of the molecular ions and the fragment ions, there is obtained a mass spectrum having a pattern inherent in compounds corresponding to the peaks. The mass spectrum is compared with a library of mass spectra produced with respect to standard specimens to search for a mass spectrum in the library that agrees with the mass spectrum for thereby identifying the unknown polymer.

The above conventional library searching process will be described below with respect to an example in which a pyrogram shown in FIG. 5 of the accompanying drawings is plotted as the pyrogram of an unknown polymer. According to the conventional library searching process, the total ion intensity that makes up a portion corresponding to the maximum point of a peak D is divided into individual ion intensities. Then, when the individual ion intensities are arranged in the order of masses of molecular ions and fragment ions, a mass spectrum shown in FIG. 6 of the accompanying drawings is obtained. The mass spectrum shown in FIG. 6 is then compared with a library of mass spectra produced with respect to standard specimens to search for the mass spectrum of a known polymer in the library that agrees with a high probability percentage with the mass spectrum for thereby identifying the unknown polymer.

Figure 6:
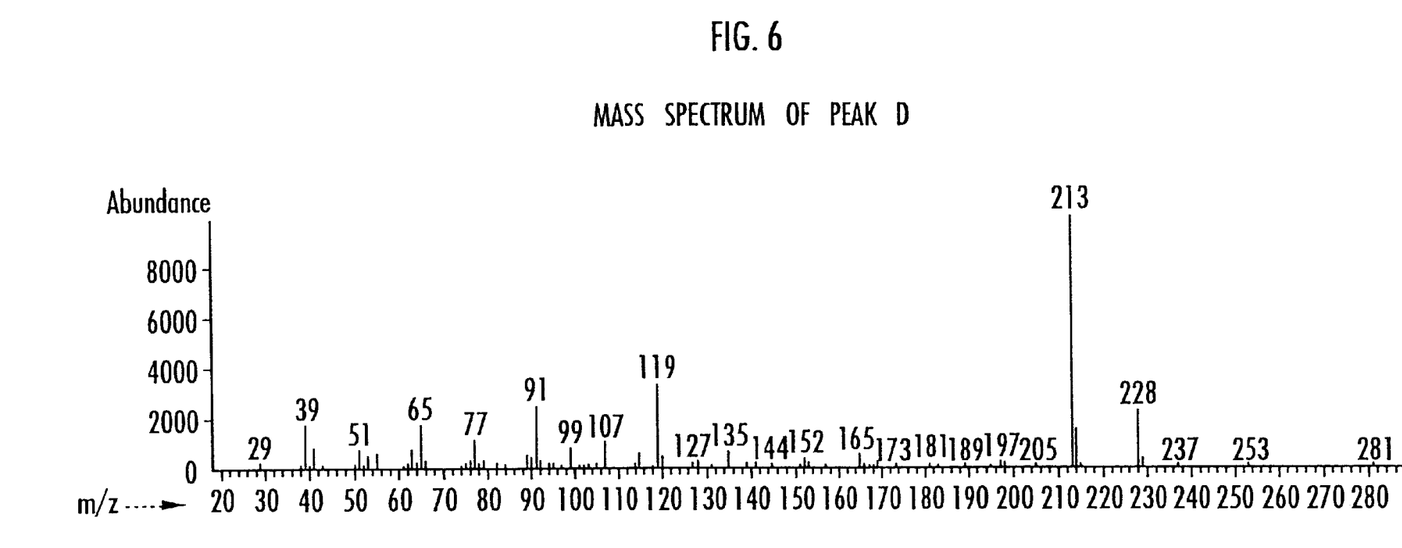
FIG. 6 is a mass spectrum showing detected data of the total ion intensity that makes up a portion corresponding to the maximum point of a peak D in the pyrogram shown in FIG. 5.
Figure 10:
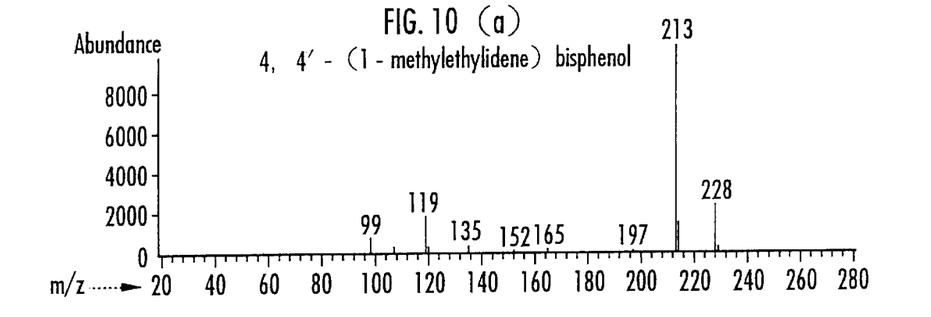

When a commercial library (WILEY) is searched for the mass spectrum shown in FIG. 6, a result is obtained as shown in FIGS. 10(a) through 10(d). FIGS. 10(a) and 10(b) show mass spectra of 4,4'-(1-methylethylidene) bisphenol. FIG. 10(c) shows a mass spectrum of p-phenyl-carbanilic acid, and FIG. 10(d) shows a mass spectrum of [1,1'-biphenyl]-3-yl-carbamic acid. The probability that a pyrolytic product corresponding to the mass spectrum shown in FIG. 6 is the same as the compounds shown in FIGS. 10(a) through 10(d) is 97%, 83%, 46%, and 43%, respectively.

According to the conventional library searching process, each of the peaks of the pyrogram shown in FIG. 5 is processed in the same manner as with the peak D to identify compounds corresponding to the peaks.

However, the conventional library searching process is time-consuming because the library needs to be searched for each one of the pyrolytic products corresponding to the peaks. Even if each one of the compounds corresponding to the peaks is identified, it requires a high level of expert knowledge, experience, and skill to determine the original polymer from the compounds thus identified.

Another process of searching for an unknown polymer uses a mass spectrum measured by directly pyrolyzing the polymer in a mass spectrometer. According to this process, one mass spectrum is obtained with respect to one polymer. Therefore, it is not necessary to search a library for individual mass spectra corresponding to peaks, and it is possible to determine an original polymer immediately from the search result.

The above process requires that a specimen introduced into the mass spectrometer be in a minute quantity of several $\mu$g or less. However, it is practically difficult to weigh such a minute quantity of specimen. Polymers that are dissolvable into solvents can be weighed in minute quantities of several $\mu$g by adjusting the concentration of the solution. However, such a weighing scheme is not applicable to crosslinked polymers that are not dissolvable into solvents.

Another problem is that when a specimen of several hundred $\mu$g that can be weighed is pyrolyzed, the ionization chamber in the mass spectrometer is contaminated and becomes useless in a short period of time.

SUMMARY OF THE INVENTION

It is therefore an object of the present invention to provide a method and apparatus, along with a recording medium with a recorded computer program, for easily identifying an unknown polymer such as a plastic or synthetic resin.

To achieve the above object, there is provided in accordance with the present invention a method of searching for an unknown polymer, comprising the steps of separating a mixture of pyrolytic products obtained by pyrolyzing an unknown polymer into the pyrolytic products, detecting ion intensities of molecule ions and fragment ions produced by ionizing the separated pyrolytic products in cycles each for a predetermined period of time, adding sets of the ion intensities of the molecule ions and the fragment ions detected in the cycles into total ion intensities, interconnecting maximum levels of the total ion intensities in a histogram composed of the total ion intensities arranged in the order of detection times thereof for thereby plotting a chromatogram, combining, for each ion of the same mass, the ion intensities contained in all the total ion intensities making up peaks in the chromatogram into combined data of the ion intensities of the molecular ions and the fragment ions, generating a combined mass spectrum of the unknown polymer which is composed of the combined data arranged in the order of masses of the molecular ions and the fragment ions, and comparing the generated combined mass spectrum of the unknown polymer with a library of combined mass spectra of a plurality of known polymers which are generated in the same manner as with the combined mass spectrum of the unknown polymer, for thereby searching for the combined mass spectrum of one of the known polymers which agrees with a high probability percentage with the combined mass spectrum of the unknown polymer.

In the above searching method, a mixture of pyrolytic products obtained by pyrolyzing an unknown polymer is separated into the pyrolytic products. The pyrolytic products are ionized, and ion intensities of generated molecule ions and fragment ions are detected. Then, total ion intensities as totals of the ion intensities detected in cycles each for a predetermined period of time are calculated, and arranged in the order of detection times thereof thereby to generate a chromatogram of the unknown polymer.

The peaks in the chromatogram which correspond to the pyrolytic products and which are formed at respective times required to separate them (retention times) represent clusters of the total ion intensities. Each of the total ion intensities may contain molecule ions or fragment ions of the same mass. Therefore, the ion intensities included in all the total ion intensities making up the peaks are combined, for each ion of the same mass, to produce combined data.

The combined data are arranged in the order of the masses of the molecule ions and the fragment ions thereby to obtain a combined mass spectrum of the unknown polymer. The combined mass spectrum corresponds to a mass spectrum which is produced by directly analyzing the mixture of pyrolytic products of the unknown polymer with a mass spectrometer, rather than separating the mixture, and arranging the ion intensities of detected molecule ions and fragment ions in the order of their masses. Consequently, the combined mass spectrum constitutes a single mass spectrum capable of representing data relative to the unknown polymer.

The combined mass spectrum of the unknown polymer is then compared with the library. The library is composed of the combined mass spectra of a plurality of known polymers which are generated in the same manner as with the combined mass spectrum of the unknown polymer. The library contains combined mass spectra generated with respect to peaks in certain ranges in the chromatograms of the known polymers, as data libraries. The peaks in the certain ranges in the chromatograms may be all or some of the peaks contained in the chromatograms.

The comparison between the combined mass spectrum of the unknown polymer with the library searches for the combined mass spectrum of one of the known polymers which agrees with a high probability percentage with the combined mass spectrum of the unknown polymer. The unknown polymer is thus identified as the known polymer whose combined mass spectrum agrees with a high probability percentage with the combined mass spectrum of the unknown polymer.

An apparatus for searching for an unknown polymer according to an aspect of the present invention comprises pyrolyzing means for pyrolyzing a specimen to generate a mixture of pyrolytic products, a separating column for separating said mixture into the pyrolytic products, a mass spectrometer for detecting ion intensities of molecule ions and fragment ions of the separated pyrolytic products, chromatogram generating means for generating a chromatogram from the ion intensities of the molecule ions and the fragment ions, combining means for generating a combined mass spectrum of the unknown polymer, library memory means for generating and storing a library of combined mass spectra of a plurality of known polymers, searching means for searching the library and outputting a search result. The method for searching for an unknown polymer according the present invention can effectively be carried out by the above apparatus.

An apparatus for searching for an unknown polymer according to another aspect of the present invention comprises library memory means for storing a library of combined mass spectra of a plurality of known polymers, detected data memory means for storing ion intensities of molecule ions and fragment ions of an unknown polymer as detected data, chromatogram generating means for generating a chromatogram based on total ion intensities obtained from the detected data, combining means for generating a combined mass spectrum of the unknown polymer, and searching means for comparing the library with the combined mass spectrum of the unknown polymer to search for the combined mass spectrum of the unknown polymer. The above apparatus may comprise a personal computer.

If the apparatus for searching for an unknown polymer comprises a personal computer, then a recording medium storing an application program executable by the personal computer may be employed. The recording medium records therein a process comprising the steps of storing ion intensities of molecule ions and fragment ions of an unknown polymer as detected data, generating a chromatogram based on total ion intensities obtained from the detected data, generating a combined mass spectrum of the unknown polymer, and comparing the library with the combined mass spectrum of the unknown polymer to search for the combined mass spectrum of a known polymer which agrees with a high probability percentage with the combined mass spectrum of the unknown polymer. A recording medium which stores the library described above may also be employed. Each of these recording mediums may comprise a magnetic recording medium such as a floppy disk or the like, or an optical disk such as a CD-ROM or the like.

The above and other objects, features, and advantages of the present invention will become apparent from the following description when taken in conjunction with the accompanying drawings which illustrate a preferred embodiment of the present invention by way of example.

BRIEF DESCRIPTION OF THE DRAWINGS

FIGS. 7(*a*), 7(*b*), and 7(*c*) are combined mass spectra generated from the pyrogram shown in FIG. 5;

FIGS. 9(*a*) and 9(*b*) are combined mass spectra generated from the pyrogram shown in FIG. 8; and FIGS. 10(*a*) through 10(*d*) are mass spectra that have been searched for with respect to the mass spectrum shown in FIG. 6.

DETAILED DESCRIPTION OF THE PREFERRED EMBODIMENT

Figure 1:
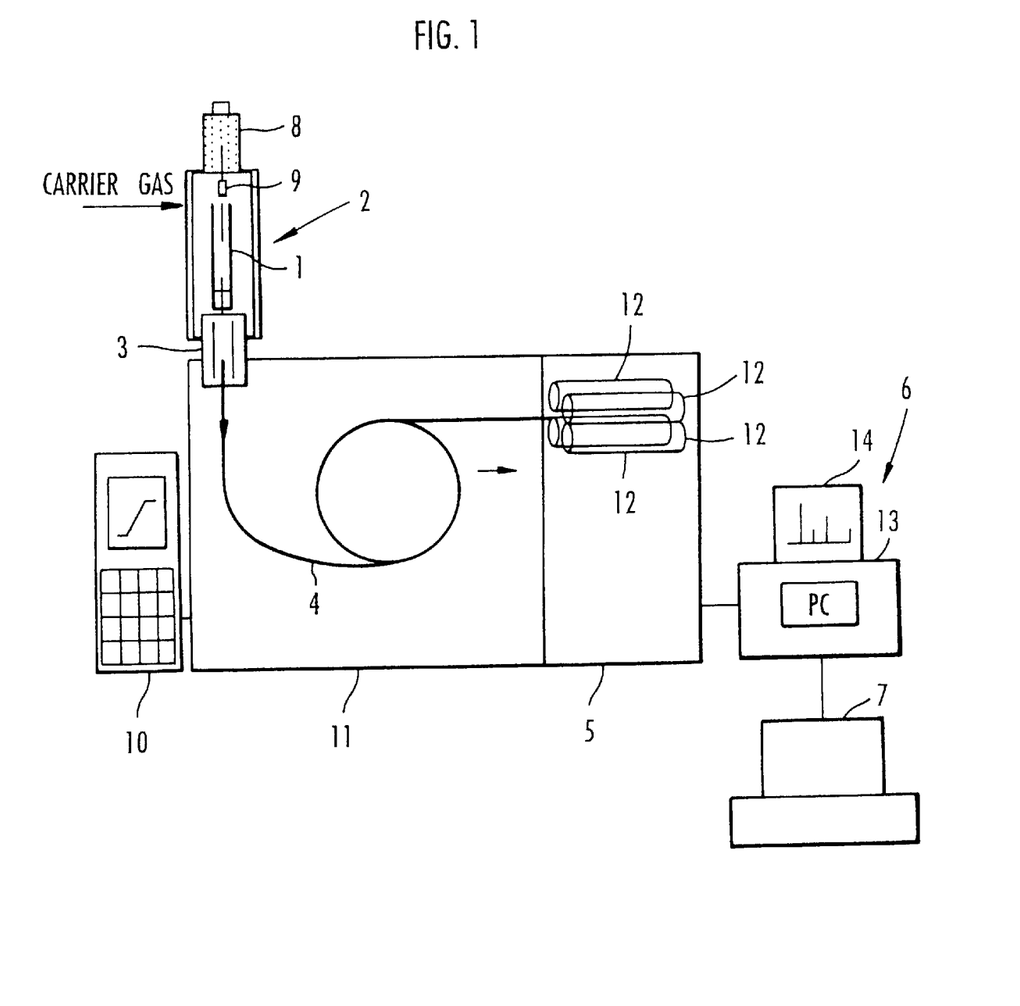
FIG. 1 is a diagram showing a system arrangement of an apparatus for searching for an unknown specimen according to the present invention.

As shown in FIG. 1, an apparatus for searching for an unknown specimen according to the present invention generally comprises a pyrolizer 2 having a pyrolyzing furnace 1, a capillary column 4 connected to the pyrolizer 2 by an inlet port 3, and a mass spectrometer 5 connected to the capillary column 4. The apparatus also includes a personal computer system 6 for being supplied with detected data from the mass spectrometer 5 and a printer 7 as an output means connected to the personal computer system 6.

The pyrolizer 2 has a specimen inlet 8 for introducing a specimen contained in a specimen cup 9 into the pyrolyzing furnace 1. In the pyrolyzing furnace 1, the introduced specimen is instantaneously pyrolyzed to generate a mixture of pyrolytic products in the form of a plurality of gaseous organic compounds. The mixture of pyrolytic products is then led via the inlet port 3 into the capillary column 4 by a carrier gas which is introduced into the pyrolizer 2 via an inlet (not shown).

The capillary column 4 is housed in a temperature-controlled chamber 11 which is controlled by a temperature controller 10. When the temperature in the temperature-controlled chamber 11 is increased from a low temperature to a high temperature by the temperature controller 10, the mixture in the temperature-controlled chamber 11 is separated into pyrolytic products successively from a compound having a low boiling point to a compound having a high boiling point, and the separated pyrolytic products are led into the mass spectrometer 5. The capillary column 4 may comprise a capillary column of fused silica or a capillary column of metal.

In the mass spectrometer 5, electrons are applied to the pyrolytic products in the form of gaseous organic compounds introduced from the capillary column 4 in cycles each for a predetermined period of time to generate molecular ions and fragment ions. The molecular ions and fragment ions which correspond to mass/charge (m/z) ratios in a predetermined range are scanned to detect intensities of the molecular ions and fragment ions. One set of ion intensities is obtained in each scanning cycle for the predetermined period of time. The mass spectrometer 5 shown in FIG. 1 comprises a quadrupole mass spectrometer. However, the mass spectrometer 5 may instead comprise a sector-type mass spectrometer.

Figure 2:
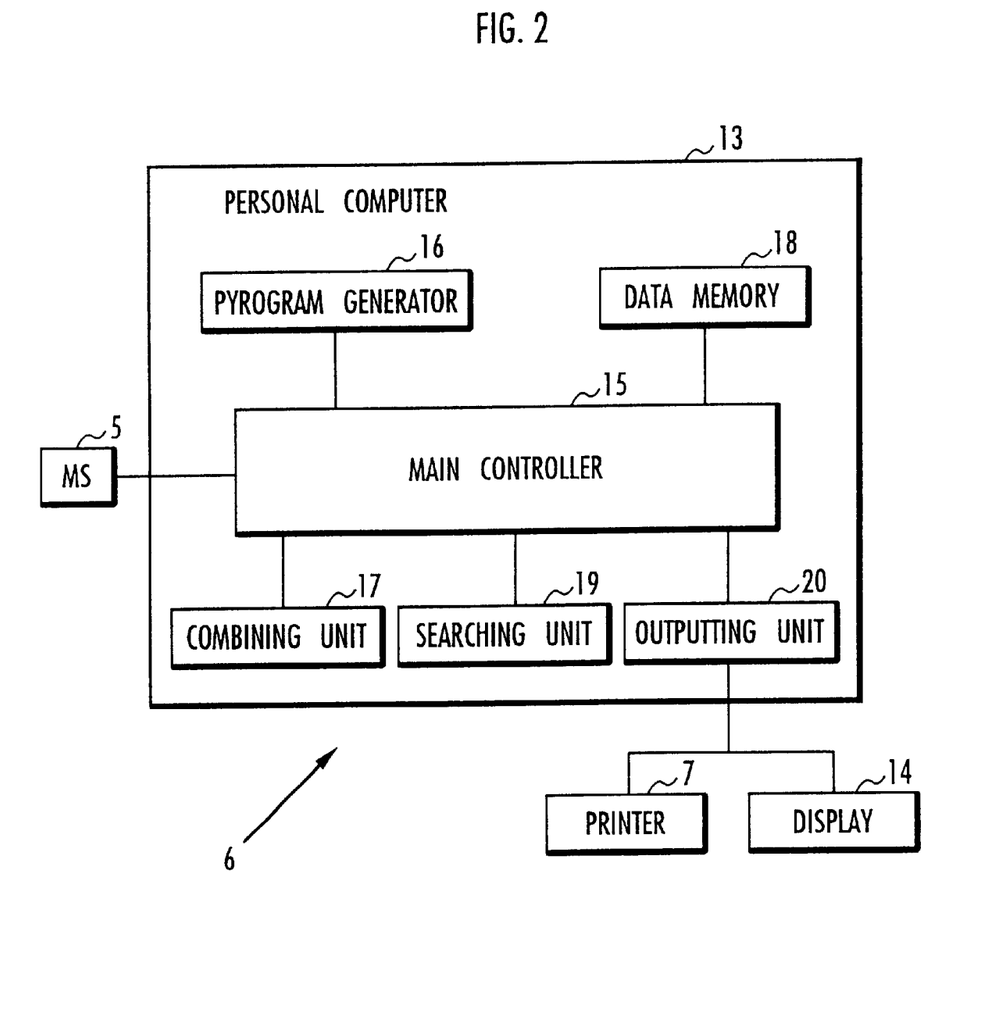
FIG. 2 is a block diagram of a personal computer system in the system arrangement shown in FIG. 1.

As shown in FIGS. 1 and 2, the personal computer system 6 comprises a personal computer 13 and a display unit 14. The personal computer 13 comprises a main controller 15 comprising a CPU, a RAM, a ROM, etc., a pyrogram generator 16, a combining unit 17, a data memory 18, a searching unit 19, and an outputting unit 20.

The personal computer system 6 controls the pyrogram generator 16, the combining unit 17, the data memory 18, the searching unit 19, and the outputting unit 20 according to a processing sequence stored in the main controller 15. The processing sequence may have been read into and stored in the main controller 15. Alternatively, the processing sequence may be recorded as an application program to be executed by the personal computer system 6 in a recording medium such as a floppy disk, a CD-ROM, or the like, and may be read from the recording medium into and stored in the main controller 15.

The data memory 18 stores a library of combined mass spectra of a plurality of known polymers. The library may have been read into and stored in the data memory 18. Alternatively, the library may be recorded in a recording medium such as a floppy disk, a CD-ROM, or the like, and may be read from the recording medium into and stored in the data memory 18.

A method of searching for an unknown specimen with the apparatus shown in FIGS. 1 and 2 will be described below.

The library stored in the data memory 18 will first be described below. The library can be constructed of data generated by sampling a plurality of known polymers with the apparatus shown in FIGS. 1 and 2.

Figure 11:
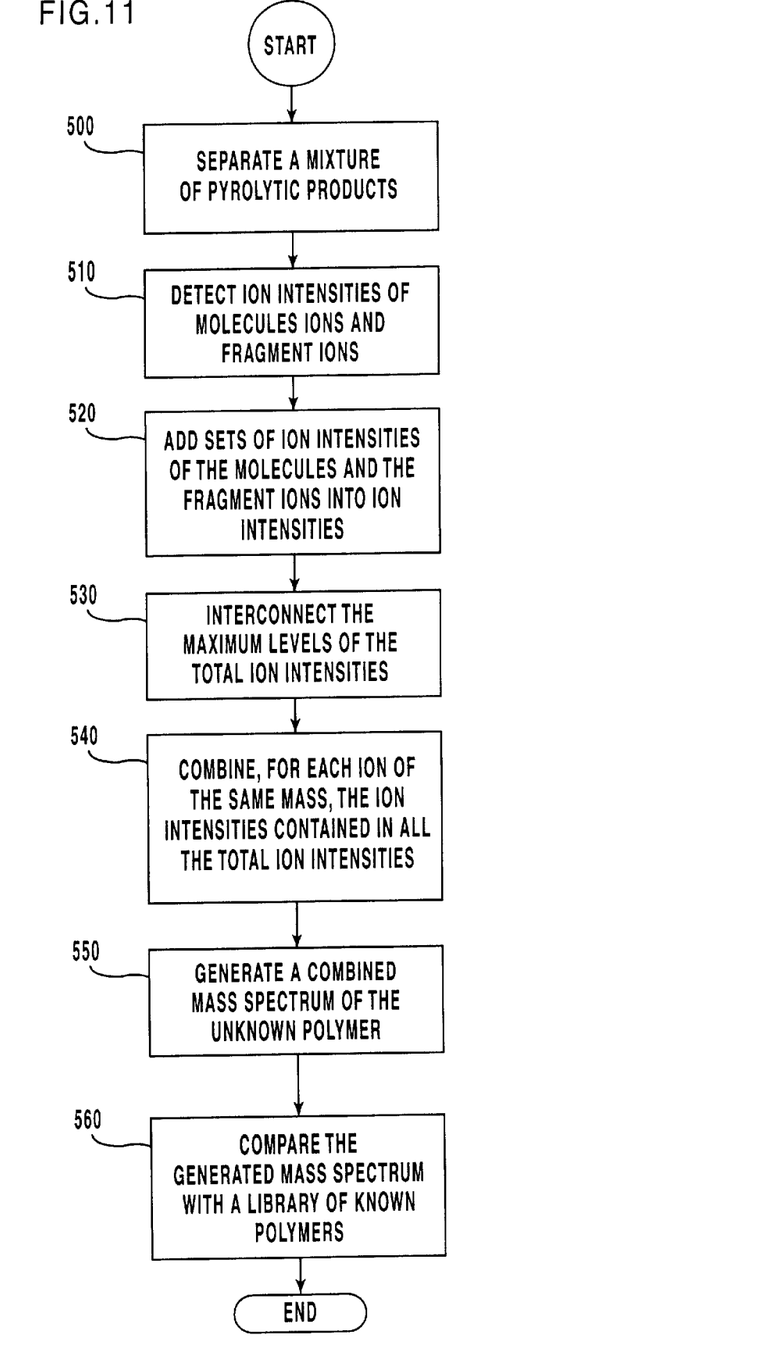
FIG. 11 is a flow chart illustrating one example of the method according to the invention.

A process of sampling data, as shown in FIG. 11, regarding a bismaleimide triazine resin (hereinafter referred to as "BT resin") represented by the following formula (1) as an example of a known polymer, with the apparatus shown in FIGS. 1 and 2 will be described below.

(1)

For sampling data regarding the above known polymer, 0.3 mg of the polymer (BT resin) is placed in the specimen cup 9, and introduced into the pyrolyzing furnace 1 from the specimen inlet 8 of the pyrolizer 2 (tradename: Double-Shot Pyrolyzer, Model PY2020D, manufactured by Frontier Laboratories Ltd.). Then, in step 500, the specimen is instantaneously pyrolyzed at a temperature of 550° C. in the pyrolyzing furnace 1. One-fiftieth of a mixture of pyrolytic products in the form of a plurality of gaseous organic compounds which are generated is divided by the inlet port 3, and introduced via the inlet port 3 into the capillary column 4 (a capillary column of metal manufactured by Frontier Laboratories Ltd.) by the carrier gas having an inlet pressure of 0.8 kg/cm$^2$). The capillary column 4 is made of stainless steel and has an inside diameter of 0.25 mm and a length of 30 m. The capillary column 4 has an inner tube surface covered with a film of 5%-phenylmethyl silicone having a thickness of 0.25 $\mu$m. The capillary column 4 is housed in the temperature-controlled chamber 11 of a gas chromatograph (tradename: GC/MS, Model 5972 manufactured by Hewlett-Packard Co.) which comprises the temperature controller 10, the temperature-controlled chamber 11, and the mass spectrometer 5.

Then, the temperature controller 10 increases the temperature in the temperature-controlled chamber 11 from 40° C. to 320° C. at a rate of 10° C. per minute to separate the pyrolytic products of the mixture with the capillary column 4. As a result, the pyrolytic products are separated successively, generally in the order from a compound having a low boiling point to a compound having a high boiling point. The separated compounds are introduced into the mass spectrometer 5 successively from the compound having a low boiling point.

In the mass spectrometer 5, the introduced compounds are irradiated with an electron beam in cycles each for 0.008 minute, thereby generating molecule ions and fragment ions inherent in the compounds. In step 510, the ions corresponding to a range of mass/charge (m/z) ratios from 10 to 450 are successively scanned to detect ion intensities of the ions. As a result, one set of ion intensities is obtained as detected data per scanning cycle of 0.008 minute.

Figure 3:
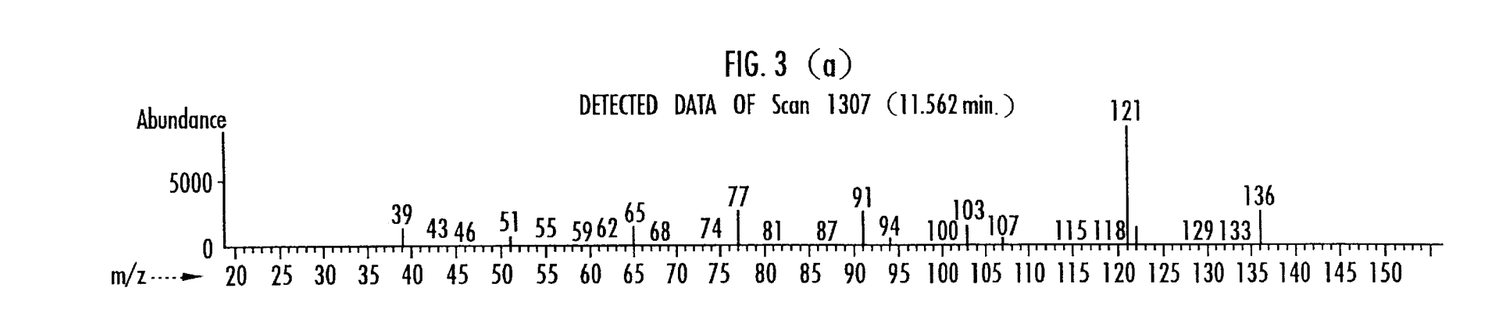
FIGS. 3(a), 3(b), 3(c) and FIG. 4 are diagrams illustrative of a process of generating a pyrolysis gas chromatogram (pyrogram) when a polymer is analyzed by the apparatus shown in FIG. 1.

One set of ion intensities with respect to the BT resin is shown in FIGS. 3(a) through 3(c). FIGS. 3(a) through 3(c) show the ion intensities of ions successively scanned in a range of mass/charge (m/z) ratios from 10 to 450 at retention times of 11.562 minutes, 11.586 minutes, and 11.611 minutes. Vertical lines indicated as histograms represent detected data indicating the ion intensities. In FIGS. 3(a) through 3(c), the numerical values accompanying the vertical lines represent m/z ratios corresponding to the vertical lines. The same definition applies to FIGS. 7(a) through 7(c) and FIGS. 9(a), 9(b).

Then, the personal computer 13 stores the detected data detected at the retention times ranging from 1 to 30 minutes in the capillary column 4 into the pyrogram generator 16 according to the processing sequence stored in the main controller 15. Thereafter, the pyrogram generator 16 of the personal computer 13 generates a pyrogram.

The pyrogram is generated as follows: In step 520, the pyrogram generator 16 adds the detected data (ion intensities) obtained in the previous scanning cycles to a set of ion intensities obtained in each cycle of 0.008 minutes producing total ion intensities, which are arranged in the order of their detection times as shown in FIG. 4.

For example, the ion intensities shown in FIG. 3(a) are detected at the retention time of 11.562 minutes, and correspond to the 1307th scanning cycle. The total of the ion intensities indicated by the vertical lines in FIG. 3(a) is represented by a total ion intensity $d_{1307}$ at the position corresponding to the retention time of 11.562 minutes in FIG. 4.

Figure 4:
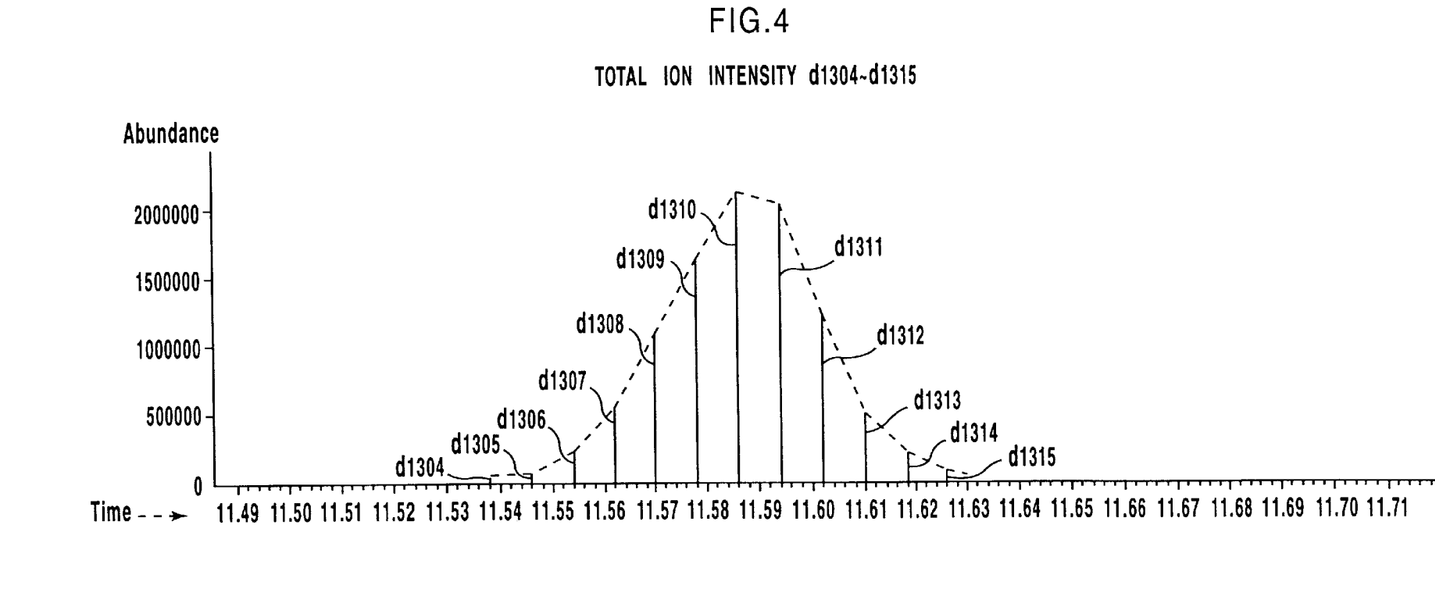

As a result, as shown in FIG. 4 with respect to a range from the retention time of 11.538 minutes to the retention time of 11.626 minutes, there is plotted a histogram composed of total ion intensities $d_{1304}$–$d_{1315}$ arranged in the order of detection times, which are produced by adding the ion intensities detected in the 1304th through 1315th scanning cycles. In step 530, a peak indicated by the broken lines is generated by interconnecting the vertexes or maximum levels of-the total ion intensities shown in FIG. 4.

The pyrogram generator 16 carries out the same operation at the retention times ranging from 1 to 30 minutes as in the range from the retention time of 11.538 minutes to the retention time of 11.626 minutes, thereby plotting a pyrogram shown in FIG. 5. The peak indicated by the broken lines in FIG. 4 is enlarged from a peak B in FIG. 5.

In step 540, the combining unit 17 combines the ion intensities, for the same mass, contained in the all total ion intensities of the peaks of the pyrogram shown in FIG. 5 according to the processing sequence stored in the main controller 15. Then, the combining unit 17 calculates combined data of the ion intensities of the ions.

In step 550, the combining unit 17 generates a mass spectrum composed of the calculated combined data arranged in the order of the masses of the ions. The mass spectrum composed of the calculated combined data arranged in the order of the masses of the molecule ions and the fragment ions will be referred to as "combined mass spectrum".

Each of the peaks in the pyrogram shown in FIG. 5 actually comprises a plurality of total ion intensities as shown in FIG. 4. Therefore, the combined mass spectrum uses all the total ion intensities $d_{1304}$–$d_{1315}$ making up a peak in the example shown in FIG. 4. The combining unit 17 combines, for each ion of the same mass, the ion intensities contained in all the total ion intensities making up the peaks with respect to all the peaks indicated in the pyrogram shown in FIG. 5.

Figure 7:
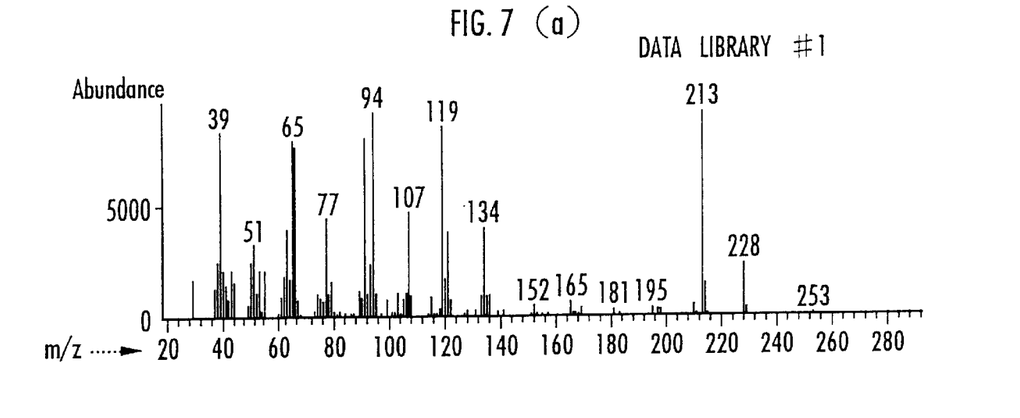

Then, the combining unit 17 arranges the combined data in the order of the masses of the ions, thus generating a combined mass spectrum as shown in FIG. 7(a). The combined mass spectrum shown in FIG. 7(a) is stored as data of the BT resin in a library stored in the data memory 18, and referred to as "data library #1". The combined mass spectrum shown in FIG. 7(a) is related to all the peaks in the pyrogram shown in FIG. 5, and corresponds to the retention times (detection times) ranging from 1 to 30 minutes.

The combining unit 17 also calculates combined mass spectra with respect to the peaks contained in a range of retention times from 1 to 15 minutes and also a range of retention times from 1 to 10 minutes in the pyrogram shown in FIG. 5. The calculated combined mass spectra are stored as data libraries #2, #3 in the library stored in the data memory 18. The combined mass spectra stored as the data libraries #2, #3 are shown in FIGS. 7(b) and 7(c), respectively.

The library stored in the data memory 18 comprises data, sampled in the same manner as with the BT resin, of known 136 polymers.

Now, a process of generating combined mass spectra of an unknown polymer with the apparatus shown in FIGS. 1 and 2 will be described below.

Combined mass spectra of an unknown polymer are generated by the same process as the above process of sampling data. In this embodiment, the BT resin employed in sampling data relative to the known polymer was also employed as the unknown polymer. However, the mixture of pyrolytic products of the BT resin as the unknown polymer was separated under a different temperature control scheme of the temperature controller 10 to obtain a pyrogram which was different from the pyrogram of the BT resin as the known polymer as shown in FIG. 5. Specifically, the temperature controller 10 increased the temperature in the temperature-controlled chamber 11 from 60° C. to 170° C. at a rate of 20° C. per minute and subsequently maintains the temperature at 170° C.

The mixture of pyrolytic products of the BT resin which was separated under the above condition was introduced into the mass spectrometer 5. Detected data from the mass spectrometer 5 were then supplied to the personal computer 13. The detected data were then processed by the pyrogram generator 16 in the same process as the above process of sampling data of the known polymer, so that a pyrogram shown in FIG. 8 was plotted.

Figure 8:
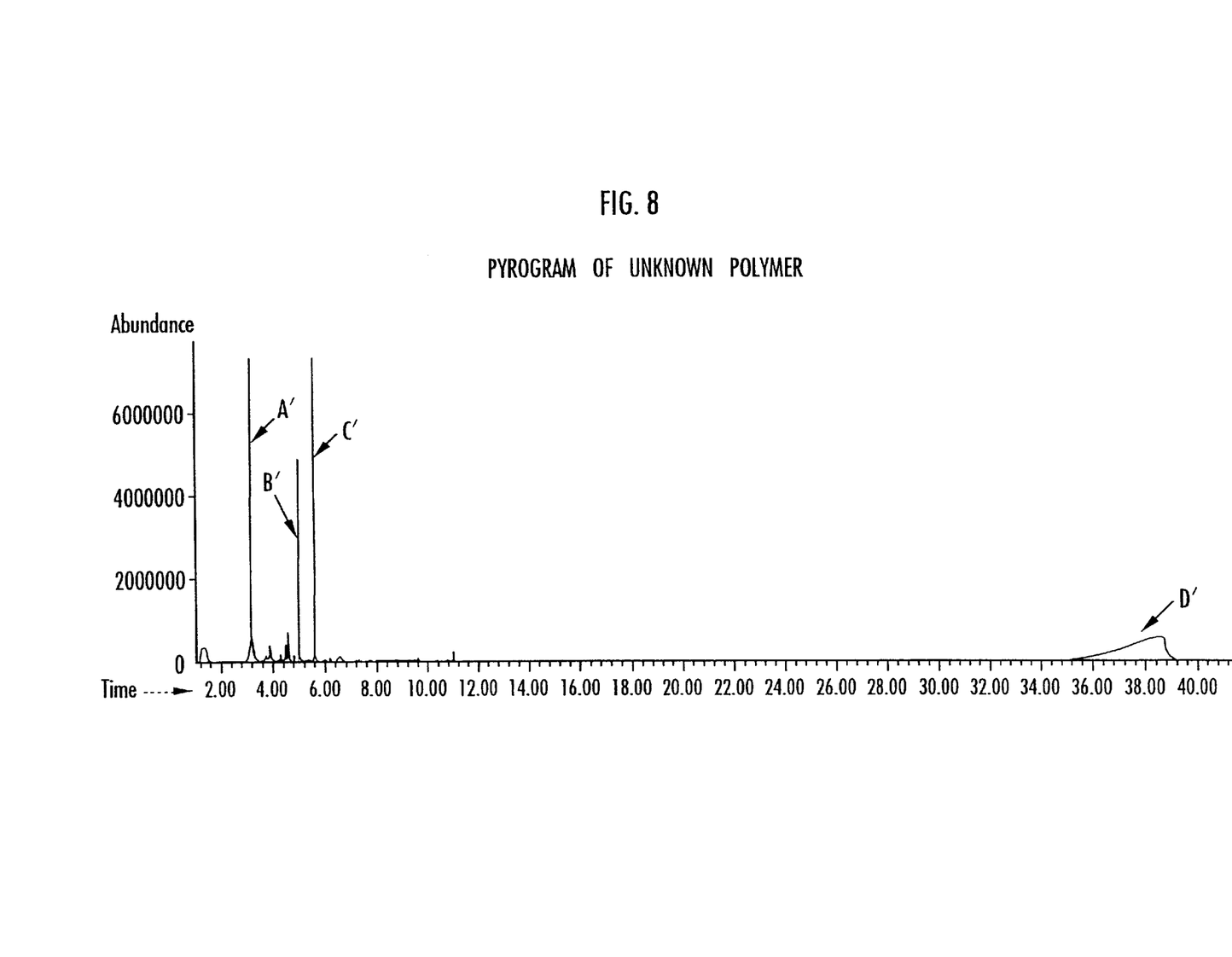
FIG. 8 is a pyrogram showing a result produced when an unknown polymer is analyzed by the apparatus shown in FIG. 1.

The pyrogram shown in FIG. 8 contained peaks A', B', C' corresponding to the peaks A, B, C in the pyrogram shown in FIG. 5, appearing between the retention times of 2 and 6 minutes. Because of the different mixture separating condition described above, however, the peak D' corresponding to the peak D in the pyrogram shown in FIG. 5 appeared between the retention times of 36 and 40 minutes, the peak D' having an increased width and a reduced height. Consequently, the pyrograms shown in FIGS. 5 and 8 showed entirely different patterns though they represented the same material. It was difficult to determine that the pyrograms shown in FIGS. 5 and 8 represent the same material from a comparison of those pyrograms.

The pyrogram shown in FIG. 8 was then processed by the combining unit 17 to produce combined mass spectra in the same manner as the sampling of data of the known polymer. The combined mass spectra plotted from the pyrogram shown in FIG. 8 are shown in FIGS. 9(a) and (b).

Figure 9:
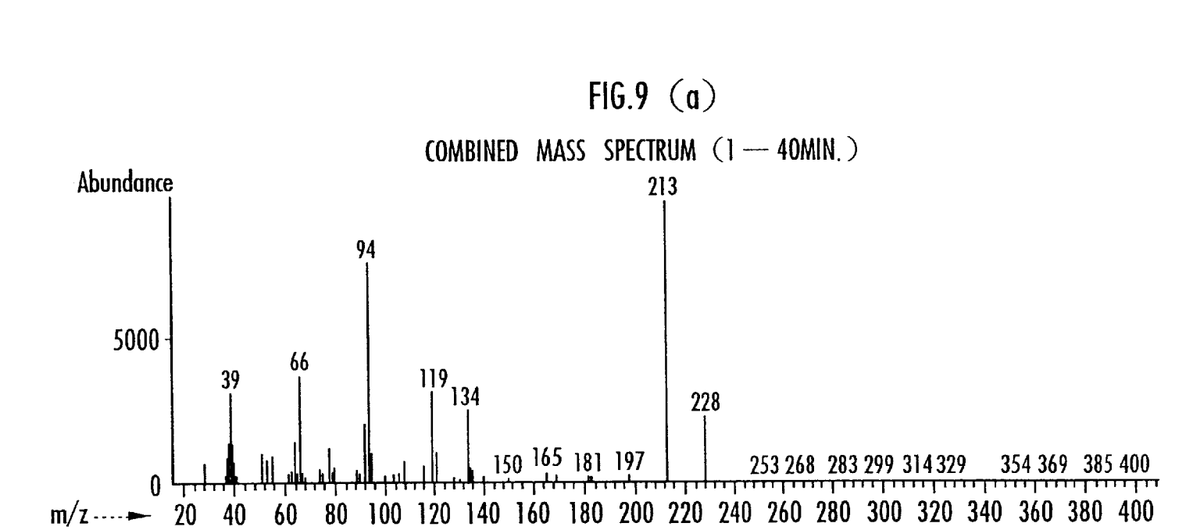

The combined mass spectrum shown in FIG. 9(a) was plotted with respect to the peaks contained in a range of retention times from 1 to 40 minutes in the pyrogram shown in FIG. 8, and the combined mass spectrum shown in FIG. 9(b) was plotted with respect to the peaks contained in a range of retention times from 1 to 10 minutes in the pyrogram shown in FIG. 8.

Then, the searching unit 19, in step 560, compared the combined mass spectra shown in FIGS. 9(a) and (b) with the library stored in the data memory 18 to search for the total mass spectrum of a known polymer which agrees with a high probability percentage with that of the unknown polymer according to the processing sequence stored in the main controller 15, as shown in Step 560.

The search result was converted into an image and displayed on the display unit 14 by the outputting unit 20 according to the processing sequence stored in the main controller 15. The image produced by the outputting unit 20 may be supplied to and printed by the printer 7.

In the illustrated embodiment, the searching 19 compared the combined mass spectrum shown in FIG. 9(a) with the library stored in the data memory 18. The search result indicated that the combined mass spectrum shown in FIG. 9(a) agreed with the data library #1 with a probability percentage of 82%, with the data library #2 with a probability percentage of 64%, and with the data library #3 with a probability percentage of 20%.

The searching unit 19 compared the combined mass spectrum shown in FIG. 9(b) with the library stored in the data memory 18. The search result indicated that the combined mass spectrum shown in FIG. 9(b) agreed with the data library #2 with a probability percentage of 78%, and with the data library #3 with a probability percentage of 64%.

The search results produced by the searching unit 19 of the combined mass spectra shown in FIGS. 10(a) and (b) are shown in the following table:

TABLE

| Unknown polymer | Search result | Probability percentage |
| --- | --- | --- |
| Combined mass spectrum shown in FIG. 10(a) (1–40 min.) | Data library #1 | 82 |
| | Data library #2 | 64 |
| | Data library #3 | 20 |
| Combined mass spectrum shown in FIG. 10(b) (1—10 min.) | Data library #2 | 78 |
| | Data library #3 | 64 |

As described above, the pyrogram shown in FIG. 8 and the pyrogram shown in FIG. 5 have completely different patterns particularly with respect to the peaks D, D'. However, as can be seen from the above Table, the combined mass spectrum shown in FIG. 9(a) agrees with high probability percentages with the data libraries #1–#3 which are combined mass spectra obtained from the pyrogram shown in FIG. 5. This is because the peaks of a pyrogram represent a cluster of total ion intensities, and the total ion intensities represent a cluster of ion intensities. Specifically, when the total ion intensities making up all peaks are used to generate a combined mass spectrum, since the ion intensities as basic constituent elements are the same, though the peaks have different shapes, the overall combined mass spectrum which is a total of the ion intensities agrees well with the data library.

As described above in detail, combined mass spectra are generated with respect to a known polymer and stored as a library, and combined mass spectra are generated with respect to an unknown polymer and then compared with the library to search for and identify the unknown polymer with a high probability percentage.

In the illustrated embodiment, the two combined mass spectra shown in FIGS. 9(a) and 9(b) are generated as combined mass spectra of an unknown polymer. However, for actually searching for an unknown polymer, a combined mass spectrum (FIG. 9(a)) with respect to all the peaks in the pyrogram or a combined mass spectrum (FIG. 9(b)) with respect to some of the peaks in the pyrogram may be selected depending on the mixture separating condition.

In the illustrated embodiment, the combined mass spectrum with respect to some of the peaks in the pyrogram is generated with respect to the peaks in the range of retention times from 1 to 10 minutes. However, a combined mass spectrum with respect to the peaks in any desired range in the pyrogram may be generated.

Although a certain preferred embodiment of the present invention has been shown and described in detail, it should be understood that various changes and modifications may be made therein without departing from the scope of the appended claims.

What is claimed is:

1. A method of searching for an unknown polymer, comprising the steps of:
   separating a mixture of pyrolytic products obtained by pyrolyzing an unknown polymer into the pyrolytic products;
   detecting ion intensities of molecular ions and fragment ions produced by ionizing the separate pyrolytic products in each cycle for a predetermined period of time;
   adding sets of ion intensities of the molecule ions and the fragment ions detected in the cycles into total ion intensities;

interconnecting maximum levels of the total ion intensities in a histogram composed of the total ion intensities arranged in the order of detection times thereof for thereby plotting a chromatogram;

combining, for each ion of the same mass, the ion intensities contained in the total ion intensities making up peaks in the chromatogram into combined data of the ion intensities of the molecular ions and the fragment ions;

generating a combined mass spectrum of the unknown polymer which is composed of the combined data arranged in the order of masses of the molecular ions and the fragment ions; and comparing the generated combined mass spectrum of the unknown polymer with a library of combined mass spectra of a plurality of known polymers which are generated in the same manner as with the combined mass spectrum of the unknown polymer, for thereby searching for the combined mass spectrum of one of the known polymers which falls within a predetermined probability percentage with the combined mass spectrum of the unknown polymer.

2. An apparatus for searching for an unknown polymer, comprising:

pyrolyzing means for pyrolyzing a specimen to generate a mixture of pyrolytic products;

a separating column for separating said mixture into the pyrolytic products;

a mass spectrometer for detecting ion intensities of molecular ions and fragment ions produced by ionizing the separated pyrolytic products in each cycle for a predetermined period of time;

chromatogram generating means for adding sets of the ion intensities of the molecule ions and the fragment ions detected in the cycles into total ion intensities and interconnecting maximum levels of the total ion intensities in a histogram composed of the total ion intensities arranged in the order of detection times thereof for thereby plotting a chromatogram;

combining means for combining, for each ion of the same mass, the ion intensities contained in the total ion intensities making up peaks in the chromatogram into combined data of the ion intensities of the molecular ions and the fragment ions, and generating a combined mass spectrum of the unknown polymer which is composed of the combined data arranged in the order of masses of the molecular ions and the fragment ions;

library memory means for generating and storing a library of combined mass spectra of a plurality of known polymers which are generated in the same manner as with the combined mass spectrum of the unknown polymer;

searching means for searching said library for the combined mass spectrum of one of the known polymers which falls within a predetermined probability percentage with the combined mass spectrum of the unknown polymer; and outputting means for outputting a search result produced by said searching means.

3. An apparatus for searching for an unknown polymer, comprising:

library memory means for storing a library of combined mass spectra of a plurality of known polymers which are generated by separating a mixture of pyrolytic products obtained by pyrolyzing each of the known polymers into the pyrolytic products, detecting ion intensities of molecular ions and fragment ions produced by ionizing the separated pyrolytic products in each cycle for a predetermined period of time, adding sets of ion intensities of molecular ions and fragment ions detected in the cycles into total ion intensities, interconnecting maximum levels of the total ion intensities in a histogram composed of the total ion intensities arranged in the order of detection times thereof for thereby plotting a chromatogram, combining, for each ion of the same mass, the ion intensities contained in the total ion intensities making up peaks in a predetermined range in the chromatogram into combined data of the ion intensities of the molecular ions and the fragment ions, and generating a combined mass spectrum of the known polymer which is composed of the combined data arranged in the order of masses of the molecular ions and the fragment ions;

detected data memory means for storing ion intensities of molecule ions and fragment ions as detected data which are generated by separating a mixture of pyrolytic products obtained by pyrolyzing an unknown polymer into the pyrolytic products, and detecting ion intensities of molecular ions and fragment ions produced by ionizing the separated pyrolytic products in cycles each for a predetermined period of time;

chromatogram generating means for generating a chromatogram by adding sets of the ion intensities of the molecular ions and the fragment ions detected in the cycles into total ion intensities and interconnecting maximum levels of the total ion intensities in a histogram composed of the total ion intensities arranged in the order of detection times thereof;

combining means for combining, for each ion of the same mass, the ion intensities contained in the total ion intensities making up peaks in the chromatogram into combined data of the ion intensities of the molecular ions and the fragment ions, and generating a combined mass spectrum of the unknown polymer which is composed of the combined data arranged in the order of masses of the molecular ions and the fragment ions; and searching means for comparing said library with the combined mass spectrum of the unknown polymer to search for the combined mass spectrum of one of the known polymers which falls within a predetermined probability percentage with the combined mass spectrum of the unknown polymer.

4. A recording medium storing an application program executable by a personal computer and recording therein a process comprising the steps of:

separating a mixture of pyrolytic products obtained by pyrolyzing an unknown polymer into the pyrolytic products and detecting ion intensities of molecular ions and fragment ions produced by ionizing the separated pyrolytic products in each cycle for a predetermined period of time;

adding sets of the ion intensities of the molecular ions and the fragment ions detected in the cycles into total ion intensities, and interconnecting maximum levels of the total ion intensities in a histogram composed of the total ion intensities arranged in the order of detection times thereof for thereby plotting a chromatogram;

combining, for each ion of the same mass, the ion intensities contained in the total ion intensities making up peaks in the chromatogram into combined data of the ion intensities of the molecular ions and the fragment ions, and generating a combined mass spectrum of the unknown polymer which is composed of the combined data arranged in the order of masses of the molecular ions and the fragment ions; and comparing the generated combined mass spectrum of the unknown polymer with a library of combined mass spectra of a plurality of known polymers which are generated in the same manner as with the combined mass spectrum of the unknown polymer, for thereby searching for the combined mass spectrum of one of the known polymers which falls within a predetermined probability percentage with the combined mass spectrum of the unknown polymer.

5. A recording medium storing an application program executable by a personal computer, comprising:

a library of combined mass spectra of a plurality of known polymers which are generated by separating a mixture of pyrolytic products obtained by pyrolyzing each of the known polymers into the pyrolytic products, detecting ion intensities of the molecular ions and fragment ions produced by ionizing the separated pyrolytic products in each cycle for a predetermined period of time, adding sets of ion intensities of molecular ions and fragment ions detected in the cycles into total ion intensities, interconnecting maximum levels of the total ion intensities arranged in the order of detection times thereof for thereby plotting a chromatogram, combining, for each ion of the same mass, the ion intensities contained in the total ion intensities making up peaks in a predetermined range in the chromatogram into combined data of the ion intensities of the molecular ions and the fragment ions, and generating a combined mass spectrum of the known polymer which is composed of the combined data arranged in the order of masses of the molecular ions and the fragment ions.

* * * * *